(12) United States Patent
Mullins et al.

(10) Patent No.: US 6,465,775 B2
(45) Date of Patent: Oct. 15, 2002

(54) METHOD OF DETECTING CARBON DIOXIDE IN A DOWNHOLE ENVIRONMENT

(75) Inventors: Oliver C. Mullins, Ridgefield, CT (US); Philip A. Rabbito, Milford, CT (US); Lawrence E. McGowan, Danbury, CT (US); Toru Terabayashi, Sagamihara (JP); Kazuyoshi Kegasawa, Sagamihara (JP)

(73) Assignee: Schlumberger Technology Corporation, Ridgefield, CT (US)

(*) Notice: Subject to any disclaimer, the term of this patent is extended or adjusted under 35 U.S.C. 154(b) by 31 days.

(21) Appl. No.: 09/741,575

(22) Filed: Dec. 19, 2000

(65) Prior Publication Data

US 2002/0074489 A1 Jun. 20, 2002

(51) Int. Cl.[7] ............................................. G01N 21/35
(52) U.S. Cl. .................................. 250/269.1; 250/256
(58) Field of Search ........................ 250/269.1, 256, 250/339.05, 339.11, 339.12, 339.13, 253, 255, 343, 345; 356/326, 328

(56) References Cited

U.S. PATENT DOCUMENTS

| 3,859,851 A | 1/1975 | Urbanosky | 73/155 |
|---|---|---|---|
| 4,396,259 A | 8/1983 | Miller | 351/158 |
| 4,994,671 A | 2/1991 | Safinya et al. | 250/255 |
| 5,167,149 A | 12/1992 | Mullins et al. | 73/155 |
| 5,201,220 A | 4/1993 | Mullins et al. | 73/155 |
| 5,266,800 A | 11/1993 | Mullins | 250/256 |
| 5,331,156 A | 7/1994 | Hines et al. | 250/256 |
| 5,821,537 A | * 10/1998 | Ishihara et al. | 250/339.13 |
| 5,859,430 A | 1/1999 | Mullins et al. | 250/255 |
| 6,352,110 B1 | * 3/2002 | Langseth et al. | 166/264 |

OTHER PUBLICATIONS

Badry, Rob et al. *Downhole Optical Analysis of Formation Fluids. Oilfield Review.* (Jan. 1994) pp. 21–28.
Crombie, A. et al. *Innovations in Wireline Fluid Sampling. Oilfield Review.* (Autumn 1998) pp. 26–41.
Ireland, Tim. *The MDT Tool: A Wireless Testing Breakthrough. Oilfield Review.* (Apr. 1992) pp. 58–65.

* cited by examiner

Primary Examiner—Constantine Hannaher
Assistant Examiner—Otilia Gabor
(74) Attorney, Agent, or Firm—Jody Lynn DeStefanis; William B. Batzer; John J. Ryberg

(57) ABSTRACT

Methods of detecting carbon dioxide in downhole environments are provided. Near-infrared light is transmitted through a gas downhole. Indications of near-infrared absorptions are detected from the gas and used to determine the presence of carbon dioxide.

17 Claims, 5 Drawing Sheets

METHOD OF DETECTING CARBON DIOXIDE IN A DOWNHOLE ENVIRONMENT

BACKGROUND

Optical analyses of fluids, including gases, are well known, and various optical and spectroscopic techniques have been applied in oilfield environments to analyze formation fluids. For example, U.S. Pat. No. 4,994,671 to Safinya et al. describes an apparatus and method for analyzing the composition of formation fluids. Formation fluids are drawn into a testing region and analyzed by directing light at the fluids and detecting the spectrum of transmitted and/or scattered light. The detected spectra are fit to spectra of known composition to determine the composition of the fluid sample. U.S. Pat. No. 5,266,800 to Mullins and U.S. Pat. No. 5,331,156 to Hines et al. describe applying optical density measurements to distinguish between crude oils and to analyze water and oil fractions, respectively, in, e.g., a formation flow stream obtained by a borehole tool. U.S. Pat. Nos. 5,167,149 to Mullins et al. and 5,201,220 to Mullins et al. describe a method and apparatus that involve transmitting light towards a fluid in a flow line and detecting reflected light at various angles of incidence. Information related to the Brewster angle and critical angle of in known gas volumes of formation fluids is used to categorize the fluid in the flow line as high gas, medium gas, low gas, and no gas. U.S. Pat. No. 5,859,430 to Mullins et al. describes a borehole tool and method for the downhole analysis of formation gases. When substantial amounts of gas are detected in a fluid stream, the fluid stream is diverted into a sample cell. The gaseous fluid sample is analyzed by directing light to the sample cell and detecting absorbance spectra. The detected spectra are fit to known spectra of various hydrocarbons in order to obtain information regarding the hydrocarbon composition in the gas stream.

U.S. Pat. No. 4,994,671, No. 5,266,800, No. 5,331,156, No. 5,167,149, No. 5,201,220, and No. 5,859,430 are each incorporated by reference herein in their entireties.

SUMMARY OF INVENTION

The invention provides methods of detecting carbon dioxide downhole in, for example, a borehole, a production well, or other subsurface earth formation. In one aspect, the invention provides a method of distinguishing between carbon dioxide and methane downhole. Near-infrared light is transmitted through formation gases downhole, and indications of near-infrared absorptions are detected from the formation gases. The detected indications of near-infrared absorptions are used to distinguish carbon dioxide from methane in the formation gases.

Another aspect of the invention provides a method of monitoring for carbon dioxide breakthrough in an enhanced oil recovery operation. An evaluation tool is inserted into a stream of fluid flowing in a wellbore. When gas is determined to be present in the fluid stream, near-infrared light is transmitted through the gas and indications of near-infrared absorptions are detected from the gas. The indications of near-infrared absorptions are used to determine the presence of carbon dioxide in the stream of fluid.

Further details and features of the invention will become more readily apparent from the detailed description that follows.

BRIEF DESCRIPTION OF FIGURES

The invention will be described in more detail below in conjunction with the following Figures, in which.

DETAILED DESCRIPTION

In general, the invention involves the use of near-infrared absorption spectroscopy to detect the presence of carbon dioxide in a downhole environment. The fraction of light absorbed per unit path length in a sample depends on the composition of the sample and the wavelength of the light. Thus, the amount of absorption as a function of wavelength of light, hereinafter referred to as an "absorption spectrum", has been used in the past as an indicator of the composition of the sample. However, the use of absorption spectroscopy to detect the presence of carbon dioxide in downhole environments, or to distinguish carbon dioxide from a hydrocarbon gas, such as methane, that is present in formation fluids, has not been described previously in any detail.

Figure 1:
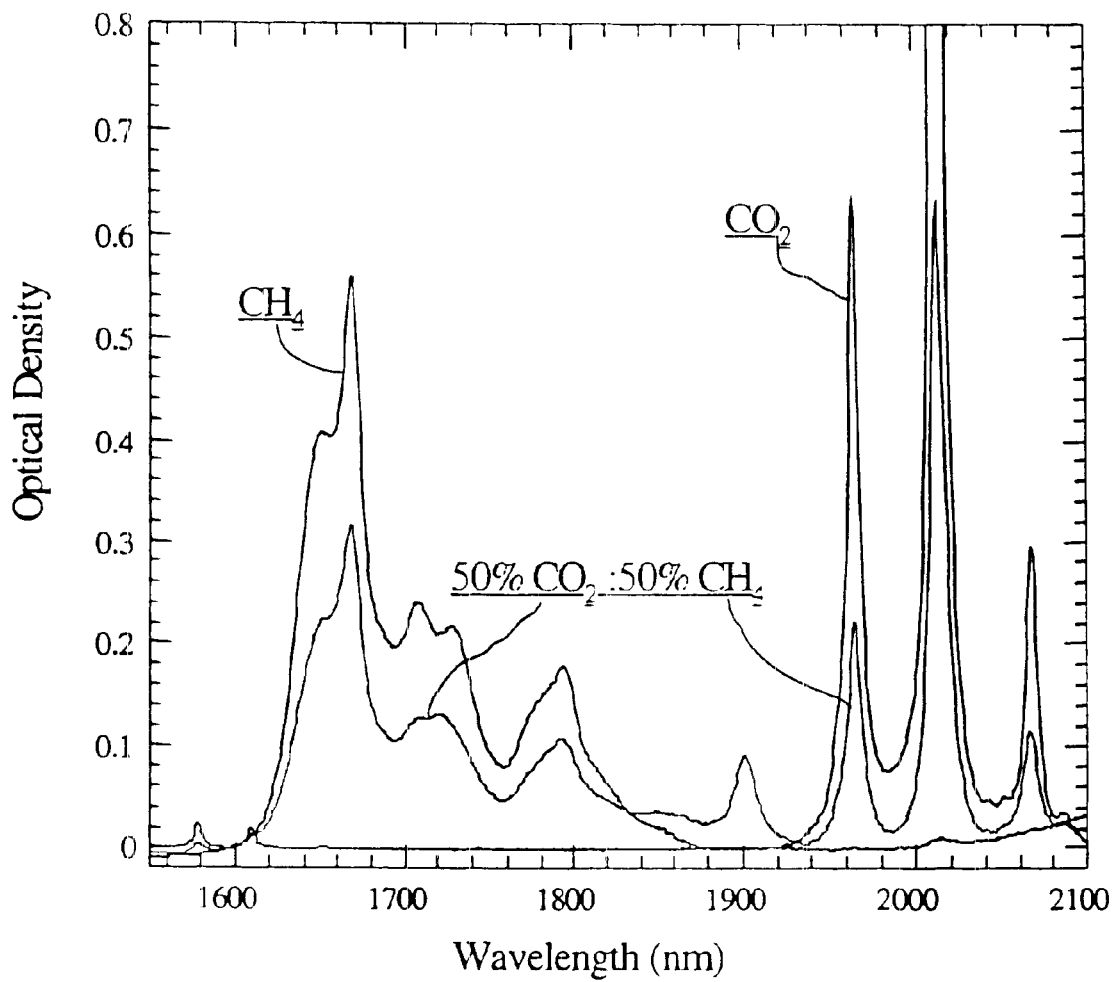
FIG. 1 shows the near-infrared absorption spectra of methane, carbon dioxide, and a 50:50 mixture by mass thereof taken at high pressure.

FIG. 1 shows the near-infrared absorption spectra of methane, carbon dioxide and a 50-50 mass mixture of methane and carbon dioxide from about 1550 nm to about 2100 nm. These absorption spectra show optical density, which is a logarithmic scale measure of the ratio of incident light to light transmitted through the sample, plotted as a function of wavelength. An optical density of zero means that all the incident light at that wavelength is transmitted through the sample and none absorbed, and an optical density of one means that about 90% of the incident light at that wavelength is absorbed.

The absorption spectrum of methane ($CH_4$) shows numerous absorption peaks in the region between about 1600 nm and about 1900 nm, with a large peak at about 1670 nm. The absorption spectrum of carbon dioxide ($CO_2$) shows very little spectral structure in this region and large absorption peaks at about 1960 nm, 2010 nm, and 2060 nm. The absorption spectrum of the 50-50 mixture shows a combination of spectral features of the methane and carbon dioxide spectra, with essentially no alteration of the wavelengths of the absorption peaks resulting from mixing the two gases. The peak at about 1900 nm is believed to be a spurious water absorption; as can be seen from FIG. 1, this spurious peak does not interfere with either the methane or the carbon dioxide absorptions and does not affect the optical analyses of the invention discussed below.

The spectra shown in FIG. 1 were taken under about 6000 psi of pressure and at room temperature. While the spectral features of absorption spectra of gases generally vary with temperature and pressure, at pressures above about 1000 psi, the absorption spectra of these gases and mixtures lose their ro-vibrational structure and the spectral features lose explicit dependence on temperature and pressure. Optical density is a function of sample density and hence will vary with pressure for gaseous samples, but varying the path length of the light through the gaseous sample (as discussed below)

can help compensate for the effects of pressure on optical density. Thus, the spectra of FIG. 1 indicate that absorption spectra acquired in downhole environments, where pressures can reach 20,000 psi and temperatures can reach over 200° C., can be used to detect carbon dioxide and to distinguish between carbon dioxide and methane downhole.

Figure 2:
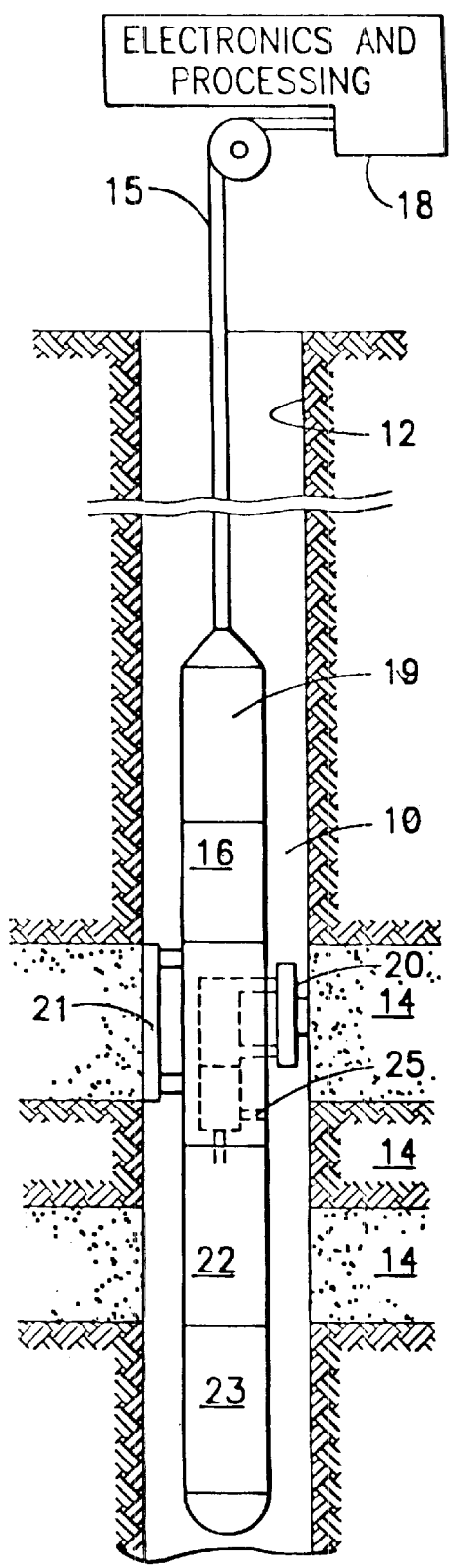
FIG. 2 illustrates a borehole apparatus for analyzing formation fluids that may be used to implement certain embodiments of the invention.

As applied to a downhole environment, the methods of the invention would be implemented using a downhole evaluation tool. FIG. 2 illustrates a borehole apparatus that may be used in implementing certain embodiments of the invention. The invention is applicable to both production logging and to borehole investigative logging, as well as monitoring of subsurface formations. For purposes of brevity, however, the description herein will be primarily directed to borehole investigative logging, and the terms "borehole" and "borehole tool" should be read throughout the specification and claims to encompass a (cased) well and a tool used in a well, as well as in a borehole.

FIG. 2 shows a borehole tool 10 for testing earth formations and analyzing the compositions of fluids from the formation 14 in accord with the invention. As illustrated, the tool 10 is suspended in the borehole 12 from the lower end of a typical multiconductor cable 15 that is spooled in a usual fashion on a suitable winch (not shown) on the formation surface. On the surface, the cable 15 is preferably electrically coupled to an electrical control system 18. The tool 10 includes an elongated body 19 which encloses the downhole portion of the tool control system 16. The elongated body 19 also carries a selectively extendable fluid admitting assembly 20 and a selectively extendable tool-anchoring member 21 which are respectively arranged on opposite sides of the body. The fluid admitting assembly 20 is equipped for selectively sealing off or isolating selected portions of the wall of borehole 12 such that pressure or fluid communication with the adjacent earth formation is established. Also included with tool 10 is a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly, the fluid analysis section, and the flow path to the collecting chambers is maintained by the electrical control systems 16 and 18.

Additional details of methods and apparatus for obtaining formation fluid samples may be had by reference to U.S. Pat. No. 3,859,851 to Urbanosky and U.S. Pat. No. 4,396,259 to Miller which are hereby incorporated by reference herein. It should be appreciated, however, that it is not intended that the invention be limited to any particular method or apparatus for obtaining the formation fluids.

Figure 3:
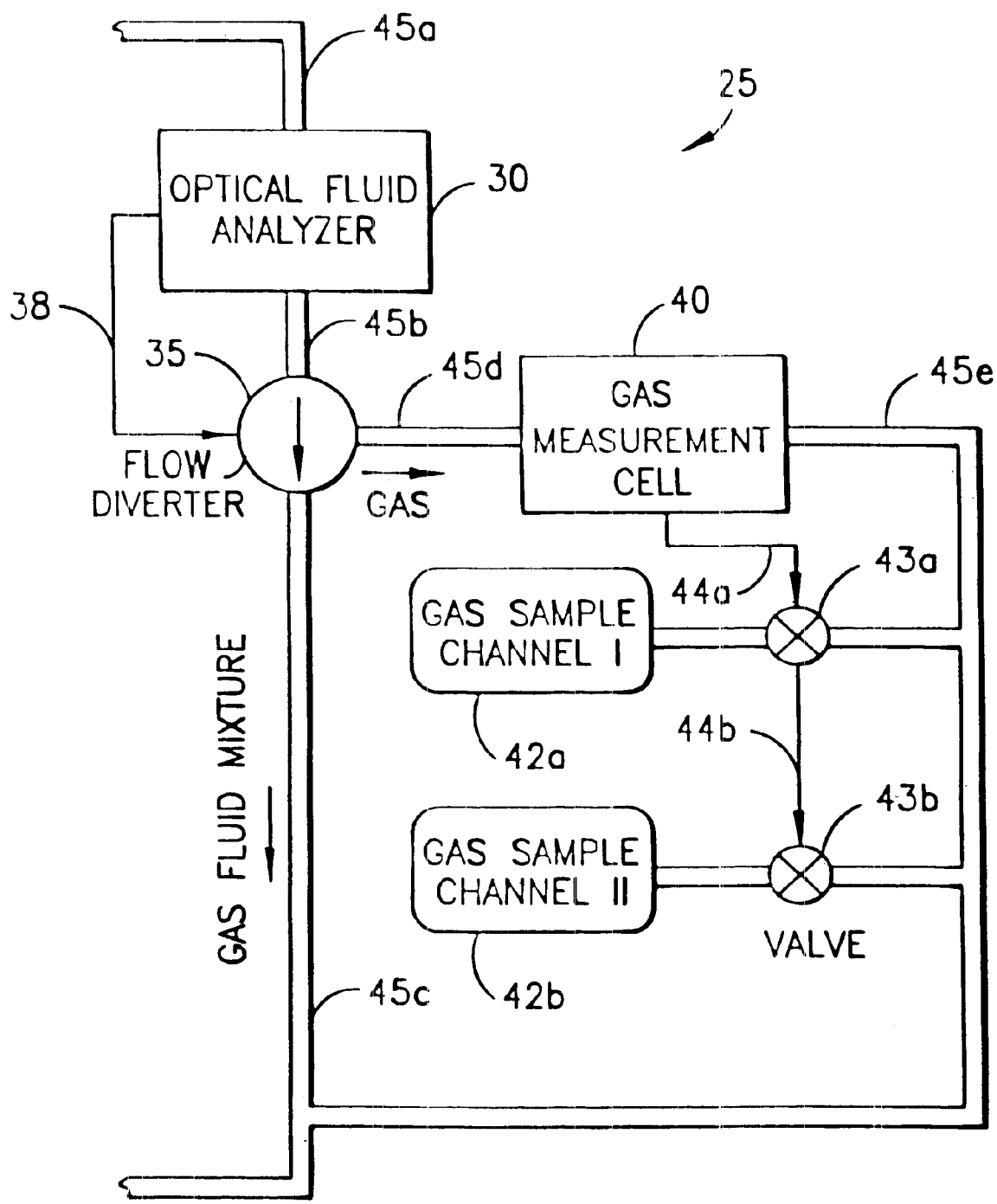
FIG. 3 shows a schematic diagram of a fluid analysis module that can be used in conjunction with a borehole apparatus, such as that shown in FIG. 2, in implementing certain embodiments of the invention.

Turning to FIG. 3, a schematic diagram is seen of one embodiment of a fluid analysis module 25 of FIG. 2. As seen in FIG. 3, the fluid analysis module 25 includes an optical fluid analyzer 30, a flow diverter 35 with associated control line 38, a gas measurement cell 40, optional gas sample chambers 42a and 42b with associated valves 43a, 43b and control lines 44a, 44b, and gas and fluid flow lines 45a, 45b, 45c, 45d, and 45e. The optical fluid analyzer 30, which receives fluids from the borehole and formation via fluid flow line 45a may be an analyzer such as shown and described in previously incorporated U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., and U.S. Pat. No. 5,331,156 to Hines et al. Thus, the optical fluid analyzer 30 is capable of distinguishing between oil, water, and gas, and as set forth in U.S. Pat. No. 5,167,149 to Mullins et al., and U.S. Pat. No. 5,201,220 to Mullins et al., is capable of categorizing the fluid sample as high gas, medium gas, low-gas, and no gas. When the fluid sample contains oil or water, the fluid sample is either optionally stored in sample fluid chambers (not shown), or expelled back into the borehole via fluid flow lines 45b and 45c.

Upon determining that the fluid sample has a high gas content, the fluid analyzer 35 provides a control signal via control line 38 to the flow diverter 35 which diverts the fluid sample via flow line 45d to the gas measurement cell 40 for analysis. While the flow diverter 35 can take many forms, preferably, it is simply embodied as an electronically controlled 2-way valve. After passing through the gas measurement cell 40, the gas may be sent to one or more gas sample chambers 43a, 43b, for storage. Valves 43a, 43b under control of the gas measurement cell 40 via control lines 44a, 44b are provided for that purpose. Alternatively, the gas may be passed via fluid flow line 45e back to fluid flow line 45c for the purpose of being expelled back into the borehole. If desired, backflow or check valves (not shown) may be provided to prevent borehole fluids from backing back into flow line 45d.

Figure 4:
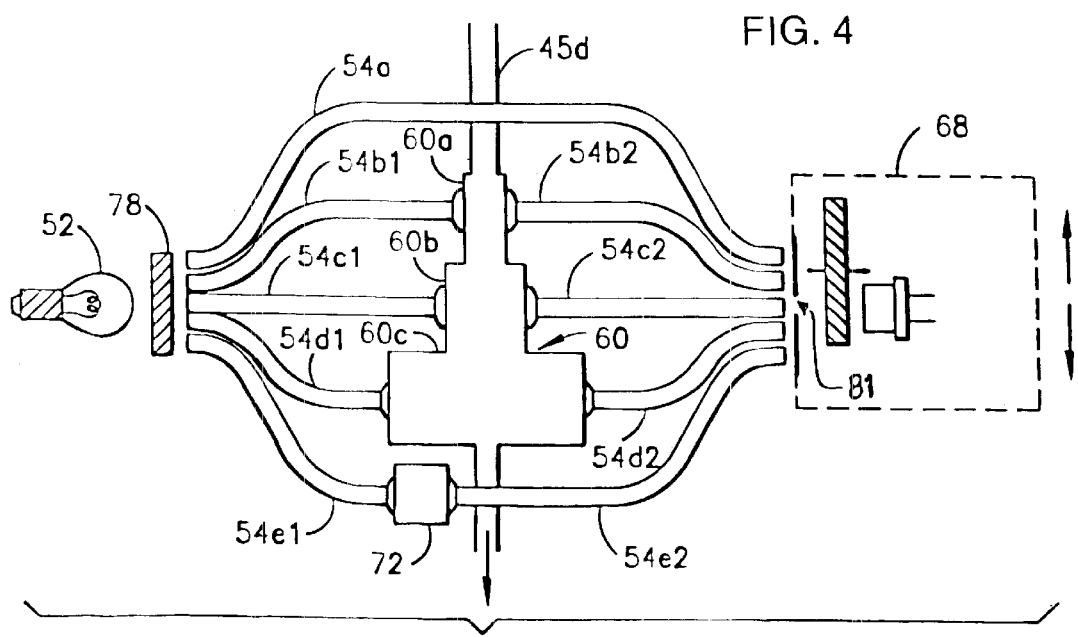
FIG. 4 shows a schematic diagram of one embodiment of a gas measurement cell that can be used in conjunction with a fluid analysis module, such as that shown in FIG. 3.

FIG. 4 shows details of one embodiment of the gas measurement cell 40 which is seen to include a light source 52, a fiber optic bundle(s) 54 (with portions 54a, 54b1, 54b2, 54c1, 54c2, 54d1, 54d2, 54e1 and 54e2), a variable path length vessel 60, including portions 60a, 60b, and 60c, a photo-detector means 68, and a known sample 72. As indicated, gas received via control line 45d is provided to the vessel 60 which includes portion 60a having a 2 mm path length (width), portion 60b having a 4 mm path length, and portion 60c having a 10 mm path length. The vessel 60 includes windows (not shown) through which the light is directed. The light is obtained from the light source 52 which provides light in the near infrared (NIR) spectrum. The light source 52 may be a narrow bandwidth light emitting diode (LED) or laser, or a broadband source, such as a tungsten halogen lamp, incandescent lamp, or the like, used in conjunction with an optical filter 78 to filter out light of other wavelengths. It should be noted that the light source 52 may reside within the cell within the borehole tool as shown in FIG. 4, or at the surface, with the light from the light source being carried downhole to the cell through optical fibers. Regardless, light from the light source 52 is carried via optical fibers 54b1, 54c1, and 54d1 to the vessel 60, and light emerging from the vessel is carried by optical fibers 54b2, 54c2, and 54d2 to the photo-detector means 68, which may reside within the cell as shown or at the surface. The photo-detector means 68 may include several arrays of photo-detectors tuned to different frequencies of interest, or a single broadband photo-detector with a filter wheel which permits a time division multiplexed determination of the frequency spectrum of the sample flowing through the vessel. Furthermore, it will be appreciated that, the light emerging from each of the portions 60a, 60b, and 60c may be sensed by different sets of photo-detectors, or as shown in FIG. 4, may be time division multiplexed to a single set of the photo-detectors through an aperture 81 which moves in conjunction with the entire photo-detector means 68. If desired, pressure sensing means may be provided for controlling which optical information is provided to the photo-detectors, as the cell portion having an appropriate path length for sensing the gas and providing a reading in a desired range will often be a function of pressure; i.e., the gas density (and hence absorbance per unit path length) varies as a function of pressure. In any event, it is generally preferable that the light provided to the photo-detector means 68 via fibers 54$b2$, 54$c3$, and 54$d2$ be separately sensed, because where the density of the gas is low, the light emerging from sample portion 60$c$ may provide a desirable signal, but the light emerging from sample portion 60$a$ will be too large and will not permit an appropriate analysis.

As previously mentioned, light from the light source is also carried by fibers 54$a$ for detection by the photo-detector means 68, and by fibers 54$e1$ to the known reference sample 72, and from the reference sample by fibers 54$e2$ to the photo-detector means 68. The provision of fibers 54$a$ for carrying light directly to the photo-detector means 68 is known in the art, and is used to cancel drift in the light source, detector, and electronics in order to provide a more robust spectral measurement. The provision of a third path through the known sample 72, however, permits compensation for shifts in actual absorption peak locations or shifts in optical filter wavelengths, yielding an even more robust determination of sample properties in the downhole environment. With the known sample, shifts in detected absorption peak wavelengths (discussed below) or shifts in optical filter wavelengths can be easily determined, thus permitting a relatively straightforward compensation for the unknown sample being analyzed.

Other embodiments and additional details of the gas measurement cell 40 are shown and described in previously incorporated U.S. Pat. No. 5,859,430 to Mullins et al.

One aspect of the invention provides methods of monitoring the presence of carbon dioxide in downhole environments. For example, carbon dioxide may be injected into a subsurface formation to facilitate the flow of oil from the formation to a producing well in an enhanced oil recovery operation, and breakthrough of carbon dioxide into the producing well would be important to detect. In another example, carbon dioxide, a greenhouse gas, may be sequestered in a subsurface formation to remove it from the atmosphere, and carbon dioxide leakage from the subsurface formation would need to be monitored. In such cases, an evaluation tool as described above, which extracts a sample of formation fluid from the formation into the tool for optical analysis, may be used. Alternatively, an evaluation tool may be injected into a flowing stream of formation fluid, e.g., into the production stream flowing in a production well, and optical analyses performed directly on the flowing stream without drawing the fluid into the tool.

Regardless of whether the evaluation tool extracts a sample of formation fluid from the formation or is injected into a flowing stream of formation fluid, when a gas is detected in the formation fluid (e.g., using the methods described in U.S. Pat. Nos. 5,167,149 and 5,201,220), near-infrared light is transmitted through the formation gas, and indications of near-infrared absorption by carbon dioxide are detected from the formation gas. In one embodiment, the indications of near-infrared absorption are detected over narrow band(s) centered at one or more wavelengths where carbon dioxide is known to absorb. As seen in the spectra of FIG. 1, carbon dioxide has strong absorption peaks at about 1960 nm, about 2010 nm, and about 2060 nm, and the presence of carbon dioxide in the formation gas may be detected using any one or more of these known absorption wavelengths. Other known carbon dioxide absorption peaks may be used, though the detection wavelength typically is selected to not overlap with any methane or other formation gas absorptions. Indications of near-infrared absorption typically also are detected at a wavelength at which neither carbon dioxide nor other formation gas absorbs in order to determine a baseline from which the carbon dioxide absorption is measured.

Individual absorption peaks may be detected using a broadband light source in conjunction with narrow band filters centered at the selected wavelengths, with the narrow band filters being placed either at the light source, to filter the light before being transmitted through the formation gas, or at the detector, to filter the light after being transmitted through the formation gas. Alternatively, a plurality of narrow band light sources, each producing a narrow band of near-infrared light centered at a selected wavelength, may be used.

Another aspect of the invention provides a method of distinguishing between carbon dioxide and methane in a downhole environment. The presence of carbon dioxide in hydrocarbon production may prove problematic for a number of reasons. When present in natural gas, carbon dioxide reduces the BTU content of the gas, making it less economical to produce. Also, if the gas is brought to the surface, carbon dioxide must be separated from the natural gas, which is a costly procedure. It would be desirable to identify and shut off carbon dioxide producing zones before the gas is brought to the surface. This requires a method to distinguish between carbon dioxide and natural gas, which is primarily methane.

As described previously, the indications of near-infrared absorptions may be detected at selected wavelengths, as opposed to scanning over a broad range of wavelengths. For example, indications of near-infrared absorption may be detected at about 1960 nm, where carbon dioxide has an absorption peak, and at about 1670 nm, where methane has an absorption peak, though other wavelengths at which carbon dioxide or methane absorbs may be used. To distinguish carbon dioxide and methane, at least three wavelengths typically are used: a first wavelength at which carbon dioxide absorbs; a second wavelength at which methane absorbs; and a third wavelength at which neither carbon dioxide or methane absorbs which is used to determine a baseline from which indications of absorption at the first and second wavelengths are measured.

Figure 5:
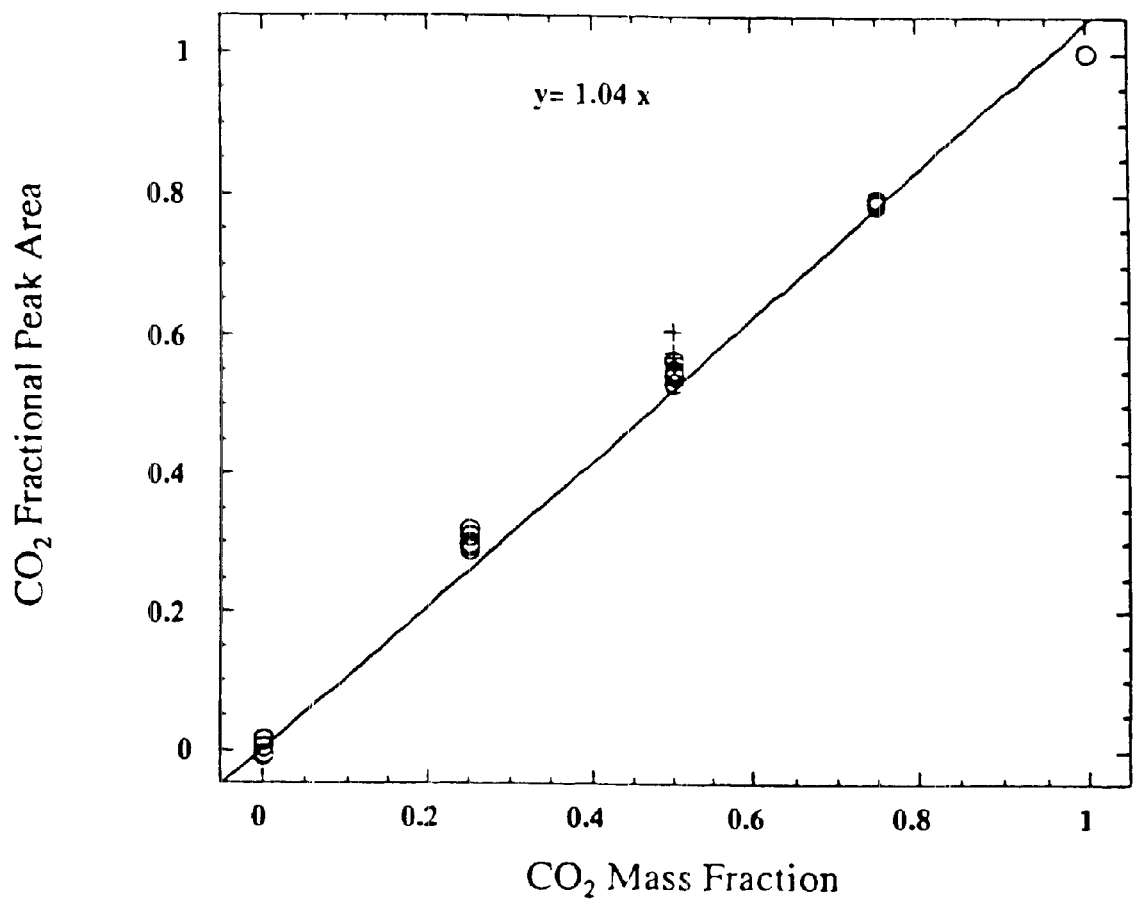
FIG. 5 contains a graph showing a correlation between fractional peak area and carbon dioxide mass fraction.

In one embodiment, spectral analysis may be accomplished by comparing the intensities of the detected absorption indications with known absorption spectra from carbon dioxide-methane gas mixtures having different relative mass fractions. The detected absorption indications may be fit to the known spectra using, e.g., a least mean squares fitting, multivariate analysis, etc. In another embodiment, the detected absorption indications may be analyzed in terms of fractional peak areas and correlated with mass fraction using known spectral data. The graph of FIG. 5 illustrates one example of such a correlation. The carbon dioxide fractional peak area was determined as the area of the carbon dioxide peak at about 1960 nm (taken over the full peak width) divided by the sum of peak area of this peak and the methane peak at about 1670 nm (taken over a 25 nm peak width to avoid overlapping with absorption peaks of other hydrocarbons). The carbon dioxide fractional peak area calculated in this fashion shows a nearly 1:1 correlation with carbon dioxide mass fraction in the mixture (the slope of the fitted line equals about 1.04). Thus, detected absorption indications analyzed in this manner provide a direct indication of carbon dioxide mass fraction. Those of ordinary skill in the art will recognize that the methodology of this analysis may be applied to determine methane mass fraction and to determine gas mixture composition in general.

The invention has been described herein with reference to certain examples and embodiments. It will, however, be evident that various modifications and changes may be made to the embodiments described above without departing from the scope and spirit of the invention as set forth in the claims.

We claim:

1. A method for distinguishing gases from an earth formation comprising:
   transmitting near-infrared light through formation gases downhole, wherein said formation gases downhole are at a pressure of at least 1000 psi;
   detecting indications of near-infrared absorptions from the formation gases;
   using the indications of near-infrared light absorptions to distinguish between carbon dioxide and methane in the formation gases.

2. The method of claim 1, wherein near-infrared light transmitted through the formation gases is in a range of at least about 1500 nm to about 2100 nm.

3. The method of claim 1, wherein detecting indications of near-infrared absorptions by the formation gases comprises detecting indications of near-infrared absorption at a first wavelength at which carbon dioxide absorbs and at a second wavelength at which methane absorbs.

4. The method of claim 3, further comprising:
   detecting near-infrared light at a third wavelength at which neither carbon dioxide nor methane absorb; and
   using the near-infrared light detected at the third wavelength to determine a baseline for detecting indications of near-infrared absorptions.

5. The method of claim 3, further comprising:
   determining optical densities at the first wavelength and at the second wavelength; and
   comparing the optical density at the first wavelength with the optical density at the second wavelength to determine a relative mass fraction of carbon dioxide.

6. The method of claim 3, wherein the first wavelength is about 1960 nm.

7. The method of claim 1, wherein the second wavelength is about 1670 nm.

8. The method of claim 1, further comprising:
   providing an evaluation tool into a borehole;
   extracting formation gases from a region of investigation traversed by the borehole into a sample cell housed within the evaluation tool, wherein near-infrared light is transmitted through the sample cell and indications of near-infrared absorptions are detected from the sample cell.

9. The method of claim 1, further comprising:
   providing an evaluation tool into a borehole; and
   extracting formation gases from a region of investigation traversed by the borehole into a plurality of sample cells housed within the evaluation tool, the plurality of sample cells having differing widths, wherein near-infrared light is transmitted through each of the plurality of sample cells along different path lengths through the formation gases corresponding to the differing widths of the plurality of sample cells.

10. The method of claim 1, further comprising:
    providing an evaluation tool into a stream of fluid, wherein near-infrared light is transmitted through the stream of fluid and indications of near-infrared absorptions are detected from the stream of fluid.

11. The method of claim 1, further comprising:
    comparing the indications of near-infrared light absorptions with absorption spectra of known carbon dioxide-methane mixtures.

12. A method of monitoring for carbon dioxide breakthrough in an enhanced oil recovery operation comprising:
    inserting an evaluation tool into a stream of fluid flowing in a production well;
    determining when a gas is present in the stream of fluid;
    transmitting near-infrared light through the gas, wherein the gas is at a pressure of at least 1000 psi;
    detecting indications of near-infrared light through the gas;
    using the indications of near-infrared absorptions to determine the presence of carbon dioxide in the stream of fluid.

13. The method of claim 12, wherein detecting indications of near-infrared absorptions comprises detecting near-infrared light in a range of about 1900 nm to about 2100 nm.

14. The method of claim 13, wherein detecting indications of near-infrared absorptions comprising detecting near-infrared light over a narrow band centered at a wavelength selected from: about 1960 nm, about 2010 nm, and about 2060 nm.

15. A method of monitoring for carbon dioxide from a subsurface formation comprising:
    extracting a sample of a gas from around the subsurface formation, wherein said gas is at a pressure of at least 1000 psi;
    transmitting near-infrared light through the sample of the gas;
    from the sample of the gas, detecting near-infrared light at a wavelength at which carbon dioxide absorbs: and
    determining whether carbon dioxide is present in the sample of gas.

16. The method of claim 15, further comprising determining a relative mass fraction of carbon dioxide present in the sample of the gas.

17. The method of claim 16, wherein determining the relative mass fraction of carbon dioxide comprises determining a fractional peak area of a carbon dioxide absorption peak and correlating the fractional peak area with the relative mass fraction.

* * * * *